United States Patent [19]

Koshino et al.

[11] Patent Number: 5,446,208
[45] Date of Patent: Aug. 29, 1995

[54] PROCESS FOR PRODUCING ETHER ALCOHOLS BY HYDROGENOLYSIS OF CYCLIC KETAL

[75] Inventors: Junji Koshino, Wakayama; Hajime Miyabe, Chiba; Yoshiaki Fujikura, Tochigi, all of Japan

[73] Assignee: KAO Corporation, Tokyo, Japan

[21] Appl. No.: 209,277

[22] Filed: Mar. 14, 1994

[30] Foreign Application Priority Data

Mar. 15, 1993 [JP] Japan .................................. 5-053781

[51] Int. Cl.$^6$ .............................................. C07C 41/48
[52] U.S. Cl. ...................................................... 568/670
[58] Field of Search ........................................ 568/670

[56] References Cited

U.S. PATENT DOCUMENTS

| | | | |
|---|---|---|---|
| 4,088,700 | 5/1978 | Watts, Jr. | 260/611 R |
| 4,479,017 | 10/1984 | Ayusawa et al. | 568/613 |
| 4,484,009 | 11/1984 | Ghenassia et al. | 568/678 |
| 5,194,423 | 3/1993 | Koshino et al. | 512/23 |

FOREIGN PATENT DOCUMENTS 1234199 9/1967 Germany .
3224033 6/1982 Germany .

OTHER PUBLICATIONS

B. Fleming and H. Bolker, "The reduction of acetals with cobalt carbonyl catalysts", *Can. J. Chem.* vol. 54, 1976, pp. 685–694.

M. Bartok and J. Czombos, "Isomerization and Hydrogenolysis of 1,3-Dioxacycloalkanes on Metal Catalysts", *J.C.S. Chem. Comm.*, 1981, pp. 106–108.

*Primary Examiner*—Johann Richter
*Assistant Examiner*—John Peabody
*Attorney, Agent, or Firm*—Sughrue, Mion, Zinn, Macpeak & Seas

[57] ABSTRACT

A process for the production of an ether alcohol is disclosed, which comprises subjecting a cyclic ketal to hydrogenolysis in the presence of a catalyst containing palladium in an amount of from 50 to 100% by weight, based on the total active catalytic component present. According to the inventive process, ether alcohols which are useful as perfumes or raw materials for perfumes can be produced easily with low cost and high yield.

6 Claims, No Drawings

PROCESS FOR PRODUCING ETHER ALCOHOLS BY HYDROGENOLYSIS OF CYCLIC KETAL

FIELD OF THE INVENTION

This invention relates to an industrially advantageous process for the production of ether alcohols which are useful as perfumes or raw material for perfumes.

BACKGROUND OF THE INVENTION

There are a large number of oxygen-containing hydrocarbon compounds, including alcohols and esters, which are useful as perfumes. For example, ether alcohols obtained from glycols and alcohols are known as important perfumes. In the prior art production processes, these ether alcohols are produced, for example, by (1) addition reaction of a glycol compound to an olefin compound (U.S. Pat. No. 4,393,247), (2) reduction of an allyl ether hydroformyl compound (U.S. Pat. No. 4,521,634), (3) addition reaction of an alcohol with an epoxide (as disclosed in JP-A-58-159435 (U.S. Pat. No. 4,608,445); the term "JP-A" as used herein means an "unexamined published Japanese patent application") and (4) hydrogenation of an epoxide-added phenol (as disclosed in JP-A-4-217937, (corresponding to U.S. Pat. No. 5,194,423)).

However, these production processes have several problems including low production yield, too many production steps, and the necessity of using hazardous materials such as sodium hydride and the like.

In addition to the above processes, these ether alcohols are also produced by (5) hydrogenolysis of cyclic ketals or cyclic acetals prepared from ketones, aldehydes and the like. Examples of such a process include: a process in which a cyclic ketal is subjected to reduction in the presence of lithium aluminum hydride and aluminum chloride (as disclosed in *Organic Synthesis Collective*, vol.5, p.303); a process in which a cyclic ketal is subjected to hydrogenolysis in the presence of a platinum or rhodium as a catalyst (as disclosed in JP-A-54-135714 (corresponding to U.S. Pat. No. 4,088,700)); and a process in which a cyclic acetal is subjected to hydrogenolysis in the presence of palladium and phosphoric acid catalysts (as disclosed in JP-A-58-189129 (corresponding to U.S. Pat. No. 4,484,009)), cobalt carbonyl catalyst (as disclosed in *Can. J. Chem.*, vol.54, p.685 (1976)), palladium, platinum or the like catalyst (as disclosed in J.C.S. *Chem. Commun.*, 106 (1981)) or palladium catalyst (as disclosed in JP-B-1-36450 (corresponding to U.S. Pat. No. 4,479,017); the term "JP-B" as used herein means an "examined Japanese patent publication").

However, of these processes for the hydrogenolysis of cyclic ketals and cyclic acetals, the process in which lithium aluminum hydride is used has a problem from an industrial production point of view because the reagent is expensive and hazardous, while the process in which a cyclic ketal is subjected to hydrogenolysis in the presence of platinum or rhodium catalyst (as disclosed in JP-A-54-135714) can produce the ether alcohol only with a low yield. On the other hand, the processes for the catalytic hydrogenolysis of cyclic acetals are reported to be effective in producing ether alcohols with a high yield (as disclosed in JP-A-58-189129 and JP-B-1-36450), but with disadvantages in that in order to obtain a high yield it is necessary to use a large quantity of a diol as a solvent, which serves as the raw material of the acetal, and the yield greatly decreases when the reaction is carried out with a reduced amount of the diol or without the solvent (as disclosed in comparative examples in JP-A-58-189129 and the like).

Accordingly, it is an object of the present invention to provide an industrially advantageous process for the production of ether alcohols, which does not necessarily require a diol solvent and is inexpensive and highly efficient.

SUMMARY OF THE INVENTION

In view of the above, the inventors of the present invention have conducted intensive studies on the catalysts for use in the hydrogenolysis of cyclic ketals and found that ether alcohols can be obtained in unexpectedly high yield and at low cost from cyclic ketals by their hydrogenation in the presence of palladium or a catalyst containing palladium as its main active component. The present invention has been accomplished on the basis of this finding.

Particularly, according to the present invention, there is provided a process for the production of ether alcohols which comprises effecting hydrogenolysis of a cyclic ketal in the presence of a catalyst containing palladium in an amount of from 50 to 100% by weight, based on the total active catalytic component present.

Other objects and advantages of the present invention will be made apparent as the description progresses.

DETAILED DESCRIPTION OF THE INVENTION

The catalyst to be used in the present invention is a catalyst which contains palladium as its main active component, namely in an amount of from 50 to 100% by weight (to be referred simply to as "%" hereinafter). Preferably, the palladium content may be 80 to 100%. When the palladium content is smaller than 50%, it may cause a decrease in reaction yield.

The catalyst to be used in the present invention may also contain at least one other catalyst selected from ruthenium, rhodium, platinum and nickel in an amount of 0 to 50%.

The catalyst to be used in the present invention may be either the metal(s) per se or supported on a carrier. Preferably, the catalyst described above may be supported on at least one carrier selected from active carbon, alumina, silica, silica magnesia and zeolite. For example, palladium may be carried on active carbon in an amount of from 1 to 10% by weight based on the weight of the carrier. In this instance, the catalyst may have a pH value of from 3 to 11, preferably from 4 to 10. The pH value of the catalyst can be measured, for example, by suspending 2 g of the catalyst in 30 ml of distilled water, stirring the resulting suspension for 5 minutes and them measuring the pH value of the suspension by a pH meter.

The catalyst to be used in the present invention may be prepared either by separately preparing each metal catalyst and then mixing them at a desired ratio, or preparing a mixed catalyst such as a co-precipitated or alloy catalyst or the like in advance and making use of it.

The method for preparing the catalyst to be used in the present invention is not particularly restricted and conventional methods can be employed. For example, the catalyst to be used in the present invention can be prepared in a method comprising washing, drying and calcining a precipitate obtained by adding a precipitant to a mixture of an aqueous solution of each catalytic metal, or a precipitate obtained by a co-precipitation method in which a precipitant is added to an aqueous solution of the catalytic metal(s) in the presence of a carrier component; a method comprising making catalytic metal(s) be impregnated and supported onto a carrier component from a state of an aqueous solution, followed by drying and calcining; or a method comprising uniformly mixing oxides, hydroxides, carbonates and the like of the catalytic metals and then calcining the resulting mixture.

In the above described methods, the catalytic metals may be employed in the form of a water-soluble salt such as a sulfate, a nitrate, an ammonium complex salt, an acetate, an oxalate, acetylacetonato salt and chloride. Examples of the precipitant to be used in the precipitation method include aqueous alkaline solutions such as solutions of ammonia, urea, ammonium carbonate, sodium carbonate, sodium hydrogencarbonate, sodium hydroxide and potassium hydroxide.

According to the process of the present invention, the catalyst may be used in an amount of preferably from 0.005 to 20%, more preferably from 0.01 to 10%, as the total amount of active components, based on the cyclic ketal to be used as the raw material compound.

Cyclic ketals to be used as the raw material compound of the inventive process are not particularly limited and may be synthesized by any known method. Examples of such methods are disclosed, for instance, in *Shin Jikken Kagaku Koza* (New Experimental Chemistry Course), vol.14 I, pp.611–631 (1977) (published by Maruzen Co., Ltd.). In a simple example of these methods, an acid catalyst such as p-toluenesulfonic acid or the like is added to a mixture consisting of a ketone and a diol, and a dehydration reaction is carried out under reflux, using an azeotropic solvent such as benzene, toluene or the like.

A preferred example of the cyclic ketal to be used in the present invention is a compound represented by the following formula (1):

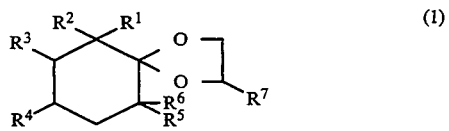

(1)

wherein $R^1$ to $R^7$ may be the same or different from one another and each represents a hydrogen atom or a straight or branched chain alkyl group having 1 to 4 carbon atoms.

The production process of the present invention is effected by hydrogenating a cyclic ketal as the raw material compound in the presence of the aforementioned catalyst. The hydrogenolysis reaction may be carried out under a hydrogen atmospheric pressure of preferably from 1 to 150 kg/cm², more preferably from 10 to 100 kg/cm², and at a reaction temperature of preferably from 50° to 300° C., more preferably from 100° to 250° C. Useful solvents include: alcohols such as methanol, ethanol, isopropyl alcohol and a diol (e.g., aliphatic diols having from 2 to 8 carbon atoms); and hydrocarbons such as hexane, cyclohexane and the like, though the process of the present invention can also be effected without using these solvents.

Ether alcohols as the compounds of interest can be isolated by subjecting the thus obtained reaction mixture to purification in the usual way such as by filtration, distillation, column chromatography and the like.

Examples of the ether alcohols produced by the present invention include those represented by the following formula (2):

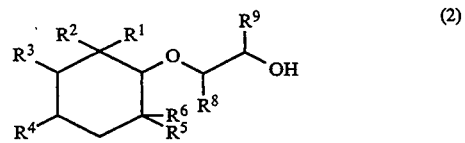

(2)

wherein $R^1$ to $R^6$ have the same meanings as defined above and one of $R^8$ and $R^9$ is a hydrogen atom and the other is a straight or branched chain alkyl group having 1 to 4 carbon atoms, which are obtained, for instance, from the cyclic ketal of the aforementioned formula (1).

Typical examples of the compounds of formula (2) are as follows:

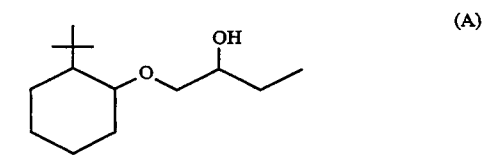

(A)

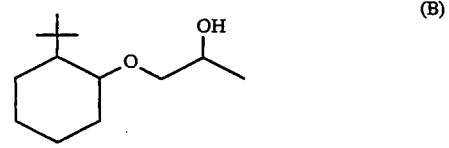

(B)

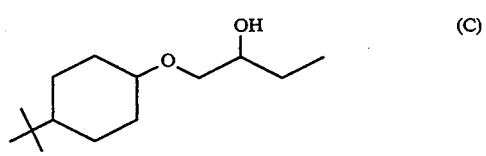

(C)

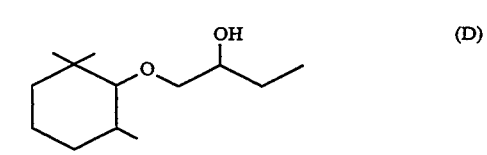

(D)

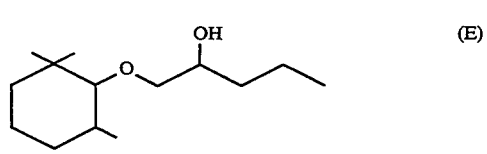

(E)

Since each of these compounds (A) to (E) has its own specific aroma of wood, camphor, earthy, amber or the like, with good tenacity, these compounds are useful as perfumes or raw materials of perfumes.

Thus, according to the present invention, ether alcohols which are useful as perfumes or raw materials of perfumes can be produced easily at low cost and in high yield. Consequently, the process of the present invention is markedly useful for the large scale production of the inventive compounds in the perfume industry and similar fields.

The following examples are provided to further illustrate the present invention. It is to be understood, however, that the examples are for purpose of illustration only and are not intended as a definition of the limits of the invention.

EXAMPLE 1

Synthesis of 1-(2-t-butylcyclohexyloxy)-2-butanol

(Compound A)

A 500 ml capacity autoclave was charged with 30 g (0.13 mol) of 6-t-butyl-2-ethyl-1,4-dioxaspiro[4.5]decane which has been prepared from 2-t-butylcyclohexanone and 1,2-butanediol, 150 g of isopropanol and 0.3 g of a catalyst of 5% palladium supported on active carbon (pH=7.6). The reaction was carried out under a hydrogen pressure of 70 kg/cm$^2$ and at a temperature of 190° C. for 20 hours until completion of the absorption of hydrogen. After the reaction, the catalyst was removed by filtration and the resulting filtrate was subjected to distillation to obtain 24.2 g of 1-(2-t-butylcyclohexyloxy)-2-butanol (b.p.=122° to 123° C./5 mmHg; yield=80%; cis:trans=66:34).

EXAMPLE 2

Synthesis of 1-(2-t-butylcyclohexyloxy)-2-butanol

(Compound A)

A 500 ml capacity autoclave was charged with 150 g (0.68 mol) of 6-t-butyl-2-ethyl-1,4-dioxaspiro[4.5]decane which has been prepared from 2-t-butylcyclohexanone and 1,2-butanediol, 1.47 g of a catalyst of 5% palladium supported on active carbon and 0.03 g of a catalyst of 5% ruthenium supported on active carbon. The reaction was carried out under a hydrogen pressure of 70 kg/cm$^2$ and at a temperature of 190° C. for 10 hours until completion of the absorption of hydrogen. In this way, 134.7 g of 1-(2-t-butylcyclohexyloxy)-2-butanol was obtained (yield=89%; cis:trans=66:34).

EXAMPLE 3

Synthesis of 1-(2-t-butylcyclohexyloxy)-2-propanol

(Compound B)

A 500 ml capacity autoclave was charged with 30 g (0.14 mol) of 6-t-butyl-2-methyl-1,4-dioxaspiro[4.5]decane which has been prepared from 2-t-butylcyclohexanone and 1,2-propanediol, 150 ml of isopropyl alcohol, 0.29 g of a catalyst of 5% palladium supported on active carbon and 0.01 g of a catalyst of 5% ruthenium supported on active carbon. The reaction was carried out under a hydrogen pressure of 70 kg/cm$^2$ and at a temperature of 190° C. for 10 hours until completion of the absorption of hydrogen. After the reaction, the catalysts were removed by filtration and the resulting filtrate was subjected to distillation to obtain 24.5 g of 1-(2-t-butylcyclohexyloxy)-2-propanol (b.p.=112° to 113° C./5 mmHg; yield=81%; cis:trans=66:34).

EXAMPLE 4

Synthesis of 1-(4-t-butylcyclohexyloxy)-2-butanol

(Compound C)

The process of Example 3 was repeated under the same reaction conditions, except that the ketal compound was changed to 30 g (0.13 mol) of 8-t-butyl-2-ethyl-1,4-dioxaspiro[4.5]decane which has been prepared from 4-t-butylcyclohexanone and 1,2-butanediol.

As the result, 21.2 g of 1-(4-t-butylcyclohexyloxy)-2-butanol was obtained (b.p.=130° to 133° C./5 mmHg; yield=90%; cis:trans=6:4).

EXAMPLE 5

Synthesis of 1-(2,2,6-trimethylcyclohexyloxy)-2-butanol

(Compound D)

The process of Example 3 was repeated under the same reaction conditions, except that the ketal compound was changed to 2 g (9 mmol) of 2-ethyl-6,6,10-trimethyl-1,4-dioxaspiro[4.5]decane which has been prepared from 2,2,6-trimethylcyclohexanone and 1,2-butanediol, the amount of each catalyst was reduced to 1/10 and the period for the completion of the reaction was changed to 20 hours.

As the result, 1.3 g of 1-(2,2,6-trimethylcyclohexyloxy)-2-butanol was obtained as purified product by a column chromatography (yield=65%).

EXAMPLE 6

Synthesis of 1-(2,2,6-trimethylcyclohexyloxy)-2-pentanol

(Compound E)

The process of Example 5 was repeated under the same reaction conditions, except that the ketal compound was changed to 2 g (9 mmol) of 6,6,10-trimethyl-2-propyl-1,4-dioxaspiro[4.5]decane which has been prepared from 2,2,6-trimethylcyclohexanone and 1,2-pentanediol.

As the result, 1.2 g of 1-(2,2,6-trimethylcyclohexyloxy)-2-pentanol was obtained (yield=60%).

COMPARATIVE EXAMPLE 1

The process of Example 1 was repeated under the same reaction conditions, except that a catalyst of 5% rhodium supported on active carbon or a catalyst of 5% ruthenium supported on active carbon was used instead of the catalyst of 5% palladium supported on active carbon. In each case, the product of interest was obtained with the yield of only 5% or less, and 90% or more of the starting material remained unreacted.

While the invention has been described in detail and with reference to specific examples thereof, it will be apparent to one skilled in the art that various changes and modifications can be made therein without departing from the spirit and scope thereof.

What is claimed is:

1. A process for producing an ether alcohol which comprises subjecting a cyclic ketal to hydrogenolysis in the presence of a catalyst containing palladium in an amount of from 50 to 100% by weight, based on the total active catalytic component present.

2. A process for producing an ether alcohol which comprises subjecting a cyclic ketal to hydrogenolysis in the presence of a catalyst containing 50 to 100% by weight of palladium and 0 to 50% by weight of at least one metal selected from ruthenium, rhodium, platinum and nickel.

3. The process for producing ether alcohol of claim 1 or 2, wherein said cyclic ketal is a compound represented by the following formula (1):

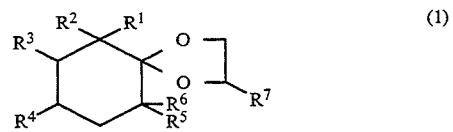

wherein $R^1$ to $R^7$ may be the same or different from one another and each represents a hydrogen atom or a straight or branched chain alkyl group having 1 to 4 carbon atoms, and said ether alcohol is a compound represented by the following formula (2):

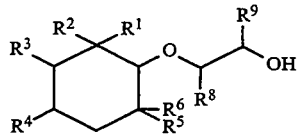
(2)

wherein $R^1$ to $R^6$ have the same meanings as defined above and one of $R^8$ and $R^9$ is a hydrogen atom and the other is a straight or branched chain alkyl group having 1 to 4 carbon atoms.

4. The process for producing an ether alcohol of claim 1 or 2, wherein said catalyst is used in an amount of from 0.005 to 20% by weight based on the cyclic ketal.

5. The process for producing an ether alcohol of claim 1 or 2, wherein said catalyst is supported on a carrier selected from active carbon, alumina, silica and zeolite.

6. The process for producing an ether alcohol of claim 1 or 2, wherein said hydrogenolysis is carried out under a hydrogen atmospheric pressure of from 1 to 150 kg/cm$^2$ and at a reaction temperature of from 50° to 300° C.

* * * * *